United States Patent [19]

McGregor et al.

[11] Patent Number: 5,002,564
[45] Date of Patent: Mar. 26, 1991

[54] SURGICAL NEEDLE CONFIGURATION WITH SPATULA GEOMETRY

[75] Inventors: Walter McGregor, Flemington, N.J.; Thomas Maurer, San Angelo, Tex.

[73] Assignee: Ethicon, Inc., Somerville, N.J.

[21] Appl. No.: 368,004

[22] Filed: Jun. 19, 1989

[51] Int. Cl.⁵ ............................................. A61B 19/00
[52] U.S. Cl. ........................................ 606/223; 112/69
[58] Field of Search ............................. 606/222–227; 112/69

[56] References Cited

U.S. PATENT DOCUMENTS

| 3,038,475 | 6/1962 | Orcutt | 606/225 X |
| 3,094,123 | 6/1963 | Kurtz | 606/223 |
| 3,636,955 | 1/1972 | Kurtz | 606/223 |
| 4,660,559 | 4/1987 | McGregor et al. | 606/226 |
| 4,699,142 | 10/1987 | Seal et al. | 606/223 |

FOREIGN PATENT DOCUMENTS

3712163A1 10/1988 Fed. Rep. of Germany.

Primary Examiner—Robert A. Hafer
Assistant Examiner—Lynda M. Cofsky
Attorney, Agent, or Firm—Paul A. Coletti

[57] ABSTRACT

A spatulated needle is provided wherein a six-sided cross-sectional portion results from a parallel or tapered pair of upper and lower surfaces connected by needle walls and a pair of fluted edges. At the tapered end of the needle, the upper surface alternates resulting in a five-sided cross-section. This improved configuration results in ease of tissue penetration, minimized tissue distortion, and minimized wound trauma. The resultant needle therefore is desirable for usage with refined surgery such as ophthalmology, microsurgery and plastic surgery.

7 Claims, 1 Drawing Sheet

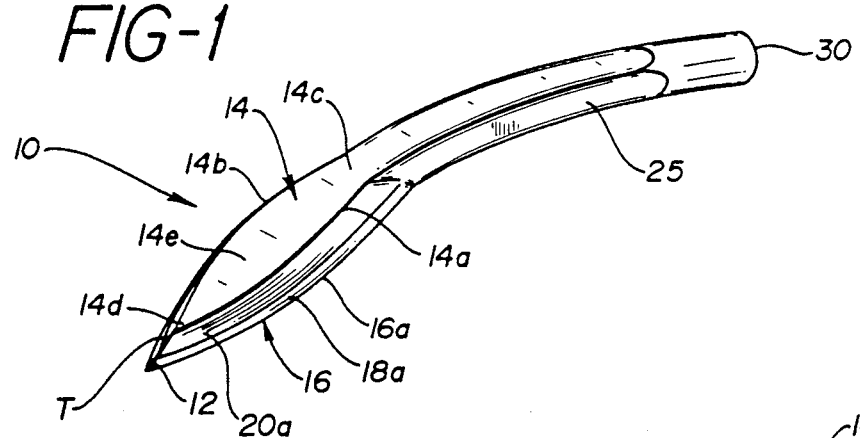
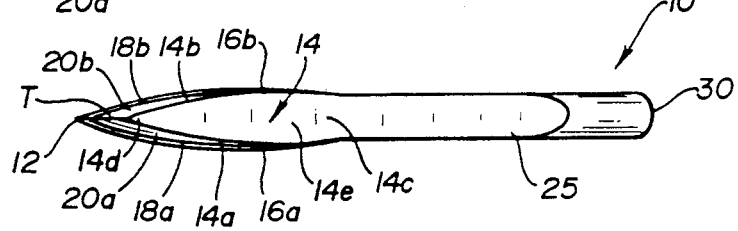
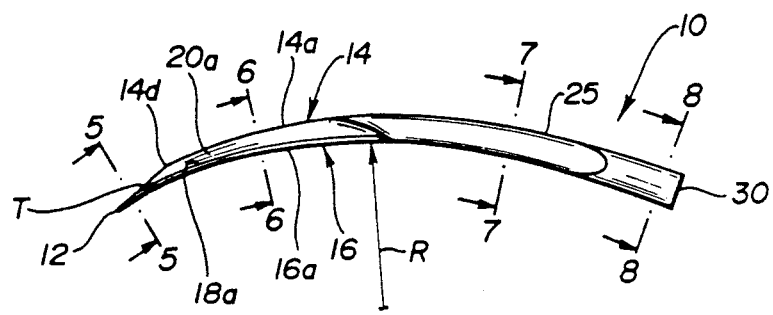
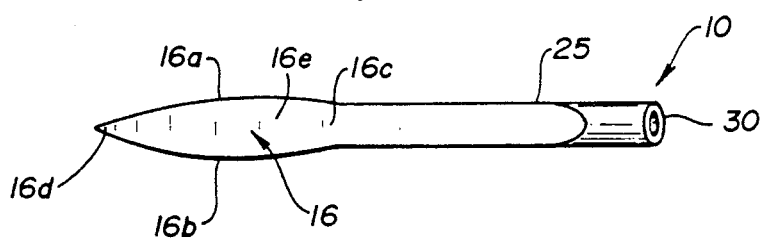
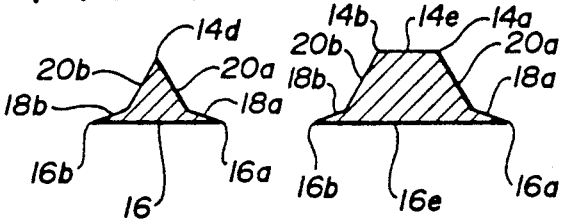
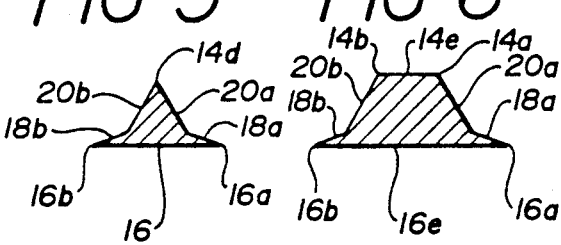
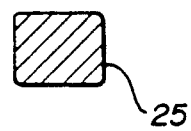
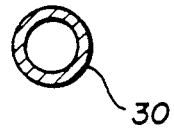

SURGICAL NEEDLE CONFIGURATION WITH SPATULA GEOMETRY

FIELD OF THE INVENTION

The present invention relates generally to improved surgical needles. More specifically, the present invention relates to surgical needles which have improved sharpness and reduced penetration resistance between needle and tissue during surgery. Most specifically, the present invention relates to a surgical needle whereby the wound opening area is reduced in order to better perform sensitive surgeries by minimizing tissue distortion and improving tissue apposition.

BACKGROUND OF THE INVENTION

The performance criteria of surgical needles can be measured in three interrelated ways. First, needle sharpness is necessary to reduce penetration resistance between needle and tissue. Greater sharpness lessens the external force required to embed the needle into tissue during surgery. Second, it is desirable to improve the needle cross-section so that the tissue opening, more commonly referred to as the wound opening site, is also reduced. As suspected, with improved penetration, the wound opening is also reduced. Third, when wound opening size is reduced, this will generally minimize the amount of tissue distortion and trauma during penetration of the needle.

With improved penetration, reduced wound opening and minimized tissue distortion, tissue apposition is generally improved As a result, finer and more approximate surgery is possible. Thus, with improved needle sharpness, it is increasingly possible to perform more specialized surgery, especially in such highly refined areas as ophthalmology, microsurgery or plastic surgery.

Generally, it has been found that the optimal needle point must have a sharply tapered end, as well as a reduced cross-section. With a sharply tapered end, it is possible to achieve penetration without maximum tissue distortion. The reduced cross-section in this case will also reduce the wound opening area. It has been found that needles triangular in cross-section have performed quite well in conjunction with tapered ends.

Nevertheless, even these triangular needles require refining in order to improve the previously stated needle sharpness criteria. That is, none of the generally triangular needles have acceptably improved all the criteria in order to configure an optimal needle. Triangular shaped cross-section needles usually sacrifice one criterion for an increased benefit in another criterion.

What is needed, therefore, is a needle with improved sharpness which also reduces penetration resistance, as well as reducing wound opening area and minimizing tissue distortion. With this optimized needle cross-section, improved tissue apposition is possible, and highly refined surgery is generally more likely.

SUMMARY OF THE INVENTION

Accordingly, it is an object of the present invention to provide a tapered needle which allows better tissue penetration.

It is further an object of the present invention to provide a needle which minimizes tissue deflection.

It is further an object of the present invention to provide a needle which improves wound area size by reducing the size of the wound areas.

It is further an object of the present invention to provide a needle which is sharp enough to perform sensitive surgery such as in the areas of ophthamology, microsurgery or plastic surgery by its improved minimized tissue distortion and improved tissue apposition.

These and other objects of the present invention are accomplished in a spatulated surgical needle having a tapered end and comprising a pair of parallel or tapered upper and lower surfaces. Each of these upper and lower surfaces contain a pair of sides and a pair of end portions. The upper surface is connected at both its sides to a needle wall which extends away from the upper surface. The lower surface is connected at each of its sides to a fluted edge. The fluted edges and needle walls angularly intersect to form a six-sided cross-section.

The lower surface is wider than the upper surface and the central portions of both upper and lower surfaces are wider than their respective end portions. This causes the surgical needle to take on a spatulated geometry. The upper surface, however, tapers at a point in advance of the lower surface. Accordingly, the upper surface at the taper forms a five-sided cross-section.

This refined needle improves tissue penetration, wound closure and tissue distortion. Therefore, the needle is more readily adapted to refined surgical techniques such as plastic surgery, microsurgery and ophthalmic surgery.

The present invention will be better understood from the figures and detailed description of the invention, in which:

DETAILED DESCRIPTION OF THE DRAWINGS

FIG. 1 is a perspective view of a spatulated surgical needle of the present invention;

FIG. 2 is a top view of a spatulated surgical needle of the present invention;

FIG. 3 is a side view of a spatulated surgical needle of the present invention;

FIG. 4 is a bottom view of a spatulated surgical needle of the present invention;

FIG. 5 is a cross-sectional view of the tapered end of the surgical needle of the present invention as seen along lines 5—5 of FIG. 3;

FIG. 6 is a cross-sectional view of the spatulated area of the surgical needle of the present invention taken along lines 6—6 of FIG. 3;

FIG. 7 is a cross-sectional view of the shaft of the spaded needle of the present invention taken along lines 7—7 of FIG. 3; and FIG. 8 is a cross-section of a hollowed-out end portion of the present invention taken along lines 8—8 of FIG. 3.

DETAILED DESCRIPTION OF THE INVENTION

As can be seen in FIG. 1, the needle 10 of the present invention has a generally spatulated shape. From FIG. 3, it can be seen that the upper surface 14 and lower surface 16, curve about radius R. Needle 10 also has a tapered end 12 which contains an angular taper T. This angular taper T can be anywhere from 1° to about 50°, with lower angular tapers T being preferred. Generally, it is desirable to have an angular taper around 20°.

In addition, upper surface 14 has a pair of sides 14a, 14b, as seen in FIG. 6. These upper surface sides 14a, 14b unite end portions 14c, 14d of the upper surface 14.

On the other hand, lower surface 16 has a pair of sides 16a, 16b. These lower surface sides 16a, 16b unite lower surface end portions 16c, 16d. Each of the upper surface 14 and lower surface 16 also have bulging central portions 14e, 16e respectively. The bulging central portion on either surface causes the spaded shape of the needle 10 as can be readily seen in FIGS. 1, 2 and 4.

As can be seen in FIGS. 5 and 6, taken in conjunction with FIG. 3, the lower surface 16, contains sides 16a, 16b, which are attached to fluted edges 18a, 18b. In turn, these fluted edges are attached to needle walls 20a, 20b which give the needle 10 its thickness. At tapered end 12, as seen in FIG. 5, the needle walls 20a, 20b meet at upper surface end portion 14d.

Generally, along the spatulated portion of the needle 10, the cross-sectional shape of the needle will be six-sided. At the tapered end 12 of the needle 10, the cross-sectional shape of the needle 10 becomes five-sided, and provides reduced cross-sectional area. This enables better tissue penetration, as well as smaller wound area.

In order to improve tissue penetration further, it is generally preferable to have each of the fluted edges contain an included angle between 1° and 35°, with about 22° being preferred. Also, in order to create adequately sharp sides, the included angle between the needle walls 20a, 20b and the upper surface 14 should be between about 100° and about 140°. Generally, about 120° is preferred. In addition, along the point created at the five-sided cross-section by needle walls 20a, 20b, the included angle should be between about 25° and about 75°, with about 60° being preferred.

Generally, as with most surgical needles, the end portion of the needle results in a rectangular-shaped cross-section 25 for needle holding stability, with a hollow end 30 for attachment of suture material. The needle itself is generally anywhere from 0.100" to about 1.5" in length and the radius R which describes the curve of the needle is anywhere from 0.030" to about 1". Of course, straight needles are also possible. The needle diameter may be anywhere from 0.001" to 0.040".

The results of the present invention are immediately apparent. That is, because of the smaller cross-sectional area presented by the pair of fluted edges united in a five-sided surface, the needle more readily penetrates tissue. Because the cross-sectional area of the needle is reduced along the remainder of the needle, wound incision area is reduced. Tissue distortion is therefore simultaneously reduced. With wound reduction, tissue apposition is also improved. Importantly, the device is readily created from such techniques as etching, coining, swaging, and grinding. The resultant improvements and ease of manufacture make the needle of the present invention quite desirable for highly refined surgery.

While the present invention has been described in conjunction with a presently preferred embodiment, it is understood by those skilled in the art that the invention is intended to encompass the presently appended claims and their equivalents, in which:

What is claimed is:

1. A spatulated surgical needle with a tapered end comprising:
    parallel upper and lower surfaces, each having a pair of sides and terminating in an end portion for attachment to a suture, said upper surface connected on both its sides to a planar needle wall;
    said lower surface connected on both sides to a planar fluted edge;
    each of said fluted edges and said needle walls meeting at an angular intersection between said upper and lower surfaces to create a six-sided cross-section.

2. The needle of claim 1 wherein said lower surface is wider than said upper surface and each of said surfaces contain a central portion wider than said end portion on each said surface.

3. The needle of claim 2 wherein said lower sides come to a point on said tapered end, resulting in a point on said needle.

4. The needle of claim 3 wherein the cross-sectional angle of said fluted edges are each between 1° and 35°.

5. The needle of claim 3 wherein said needle walls meet on said tapered end at an angle between about 25° and about 75°.

6. The needle of claim 3 wherein the angles between said needle walls and said upper surface on said needle across the six-sided cross-section are the same and are about between 100° and about 140°.

7. The needle of claim 3 wherein said upper and lower surfaces are both concave with said upper surface having a greater radius of curvature than said lower surface.

* * * * *